United States Patent
Feydo

(10) Patent No.: US 9,239,317 B2
(45) Date of Patent: Jan. 19, 2016

(54) SYSTEM AND METHOD FOR ULTRASONIC TESTING WITH A SINGLE CHANNEL ULTRASONIC TEST UNIT

(75) Inventor: Mark Howard Feydo, Reedsville, PA (US)

(73) Assignee: General Electric Company, Schenectady, NY (US)

(*) Notice: Subject to any disclaimer, the term of this patent is extended or adjusted under 35 U.S.C. 154(b) by 447 days.

(21) Appl. No.: 13/477,889

(22) Filed: May 22, 2012

(65) Prior Publication Data
US 2013/0312528 A1    Nov. 28, 2013

(51) Int. Cl.
*G01H 17/00* (2006.01)
*G01N 29/26* (2006.01)
*G01N 29/34* (2006.01)
*G08C 23/02* (2006.01)

(52) U.S. Cl.
CPC .............. *G01N 29/262* (2013.01); *G01N 29/34* (2013.01); *G08C 23/02* (2013.01); *G01N 2291/106* (2013.01)

(58) Field of Classification Search
CPC  G01N 29/262; G01N 29/34; G01N 2291/106
USPC ............ 73/632, 625, 626; 600/437, 438, 443, 600/447, 445, 449
See application file for complete search history.

(56) References Cited

U.S. PATENT DOCUMENTS

| | | | |
|---|---|---|---|
| 3,996,553 A | 12/1976 | Siems et al. | |
| 4,092,629 A | 5/1978 | Siems et al. | |
| 4,464,739 A | 8/1984 | Moorcroft | |
| 4,612,937 A * | 9/1986 | Miller | 600/441 |
| 5,329,930 A | 7/1994 | Thomas, III et al. | |
| 5,431,054 A * | 7/1995 | Reeves et al. | 73/612 |
| 5,456,256 A * | 10/1995 | Schneider et al. | 600/445 |
| 5,469,851 A | 11/1995 | Lipschutz | |
| 5,520,186 A | 5/1996 | Deitrich | |
| 5,520,187 A | 5/1996 | Snyder | |
| 5,758,649 A * | 6/1998 | Iwashita et al. | 600/459 |
| 5,827,188 A | 10/1998 | Wright et al. | |
| 5,897,501 A | 4/1999 | Wildes et al. | |
| 6,183,419 B1 | 2/2001 | Wildes | |
| 6,540,682 B1 * | 4/2003 | Leavitt et al. | 600/447 |
| 6,736,011 B2 * | 5/2004 | Zayicek et al. | 73/628 |
| 7,234,354 B2 | 6/2007 | Barshinger et al. | |
| 7,508,737 B1 | 3/2009 | Alexandru | |
| 7,804,736 B2 | 9/2010 | Alexandru | |
| 7,958,769 B2 * | 6/2011 | Langlois et al. | 73/1.82 |
| 8,333,115 B1 * | 12/2012 | Garvey et al. | 73/632 |
| 8,371,151 B2 * | 2/2013 | Langlois et al. | 73/1.82 |
| 2004/0002652 A1 * | 1/2004 | Phelps et al. | 600/437 |
| 2004/0267135 A1 | 12/2004 | Takeuchi | |

(Continued)

FOREIGN PATENT DOCUMENTS

GB    2013446 A    8/1979

OTHER PUBLICATIONS

Search Report from PCT/US13/41743 dated Aug. 1, 2013.

*Primary Examiner* — J M Saint Surin
(74) *Attorney, Agent, or Firm* — Barclay Damon, LLP

(57) ABSTRACT

A device and method for ultrasonic inspection of a test object is disclosed. A plurality of ultrasonic transducer elements and electrical pulser circuits are provided for generating and transmitting electrical pulses. The device has an interface configured to communicate with a single channel ultrasonic testing unit.

12 Claims, 2 Drawing Sheets

(56) References Cited

U.S. PATENT DOCUMENTS

| | | | |
|---|---|---|---|
| 2006/0184023 A1* | 8/2006 | Satoh | 600/437 |
| 2009/0016163 A1 | 1/2009 | Freeman et al. | |
| 2014/0116143 A1* | 5/2014 | Komsky et al. | 73/618 |

* cited by examiner

SYSTEM AND METHOD FOR ULTRASONIC TESTING WITH A SINGLE CHANNEL ULTRASONIC TEST UNIT

BACKGROUND OF THE INVENTION

The subject matter disclosed herein relates to ultrasonic testing, and more particularly, a method and system for ultrasonic testing with a single channel ultrasonic test unit.

Nondestructive testing devices can be used to inspect test objects to detect and analyze anomalies in the objects. Nondestructive testing allows an inspection technician to maneuver a probe on the surface of the test object in order to perform testing of the underlying structure. Nondestructive testing can be particularly useful in some industries, e.g., aerospace, power generation, and oil and gas transport or refining, where inspection of test objects must take place without removal of the object from surrounding structures, and where hidden anomalies can be located that would otherwise not be identifiable through visual inspection. One method of nondestructive testing is ultrasonics.

Generally, an ultrasonic testing system includes an ultrasonic probe for transmitting and receiving ultrasonic acoustic waves to and from a test object, and a probe cable for connecting the ultrasonic probe to an ultrasonic test unit that includes a display for viewing the test results. The ultrasonic test unit can also include power supply components, signal generation circuitry, amplification and processing electronics, and device controls used to adjust the instrument for the inspection. In an ultrasonic testing system, electrical pulses are fed from the ultrasonic test unit to an ultrasonic probe where they are transformed into acoustic pulses by one or more ultrasonic transducers (e.g., piezoelectric elements) in the ultrasonic probe. During operation, electrical pulses are applied to the electrodes of one or more ultrasonic transducers, thus generating ultrasonic acoustic waves that are transmitted to the test object to which the probe is coupled. Conversely, when an ultrasonic acoustic wave is reflected from the test object and contacts the surface of the ultrasonic transducer(s), it causes the transducer(s) to vibrate generating a voltage that is detected as a receive signal by the ultrasonic test unit. As the ultrasonic acoustic waves pass through the test object, various reflections, called echoes, occur as the ultrasonic acoustic wave interacts with anomalies within the test object and with the inner surface (back wall) of the test object.

When testing with a single element probe, the echo signals are typically displayed on the screen of a single channel ultrasonic test unit as an A-scan trace with echo amplitudes appearing as vertical deflections of the trace and time of flight or distance information displayed as horizontal position along the trace. When inspecting a weld, for example, if an echo is identified other than a geometry echo, that echo may indicate the presence of an anomaly in the weld. This single channel probe is often mounted on a wedge to direct the sound at an angle (e.g., from thirty to seventy degrees) to inspect different regions of the test object. In order to inspect the full volume of the object it may be necessary to scan the object several times using different angles (wedges). Inspecting the test object at several different angles can be time consuming.

A phased array ultrasonic probe has a plurality of electrically and acoustically independent ultrasonic transducers mounted in a single housing. By varying the timing of the electrical pulses applied to the ultrasonic transducers, a phased array ultrasonic probe can generate ultrasonic beams at different angles, allowing the phased array ultrasonic probe to steer the ultrasonic beam at different angles (e.g., from thirty to seventy degrees at one degree increments) through the test object to try to detect anomalies. The ultrasonic waves received at the various angles can be processed to produce a sector scan image of the test object, allowing visual identification of any anomalies. While the phased array ultrasonic probe can produce the data necessary to generate a sector scan image, and eliminate the need to rescan the test object several times with different wedges on a single element probe, the phased array ultrasonic testing unit is significantly more expensive that the single channel ultrasonic testing unit. Also, for phased array ultrasonic probes containing dozens of individual elements, the probe cable from the phased array ultrasonic testing unit to the phased array probe can be quite dense and difficult to maneuver.

The discussion above is merely provided for general background information and is not intended to be used as an aid in determining the scope of the claimed subject matter.

BRIEF DESCRIPTION OF THE INVENTION

A device and method for ultrasonic inspection of a test object is disclosed. A plurality of ultrasonic transducer elements and electrical pulser circuits are provided for generating and transmitting electrical pulses. The device has an interface configured to communicate with a single channel ultrasonic testing unit.

In one exemplary embodiment, a ultrasonic probe is disclosed. The ultrasonic probe comprises a plurality of ultrasonic transducer elements and a plurality of electrical pulser circuits for generating and transmitting electrical pulses to the ultrasonic transducer elements. A microprocessor is provided for controlling the plurality of electrical pulser circuits. An interface is configured to communicate with a single channel ultrasonic testing unit.

In another exemplary embodiment, a method for ultrasonic inspection is disclosed. A method comprises receiving a synchronization signal and controlling a plurality of electrical pulser circuits in response to the synchronization signal. Ultrasonic acoustic waves are generated in a test object that are responsive to each of the plurality of electrical pulser circuits, the ultrasonic acoustic waves corresponding to a first angle. The reflected ultrasonic acoustic waves are received from the test object and transmitted to a single channel analog signal that is representative of the received ultrasonic acoustic waves, wherein the single channel analog signal is configured to be received by a single channel ultrasonic testing unit.

In a third exemplary embodiment, a non-transitory medium storing logic that, when executed, causes a circuit to perform a method is disclosed. The method comprises receiving at least one of a synchronization signal and controlling a plurality of electrical pulser circuits in response to the synchronization signal. Ultrasonic acoustic waves are generated in a test object that are responsive to each of the plurality of electrical pulser circuits. The reflected ultrasonic acoustic waves are received from the test object and transmitted to a single channel analog signal that is representative of the received ultrasonic acoustic waves, wherein the single channel analog signal is configured to be received by a single channel ultrasonic testing unit.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description.

This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
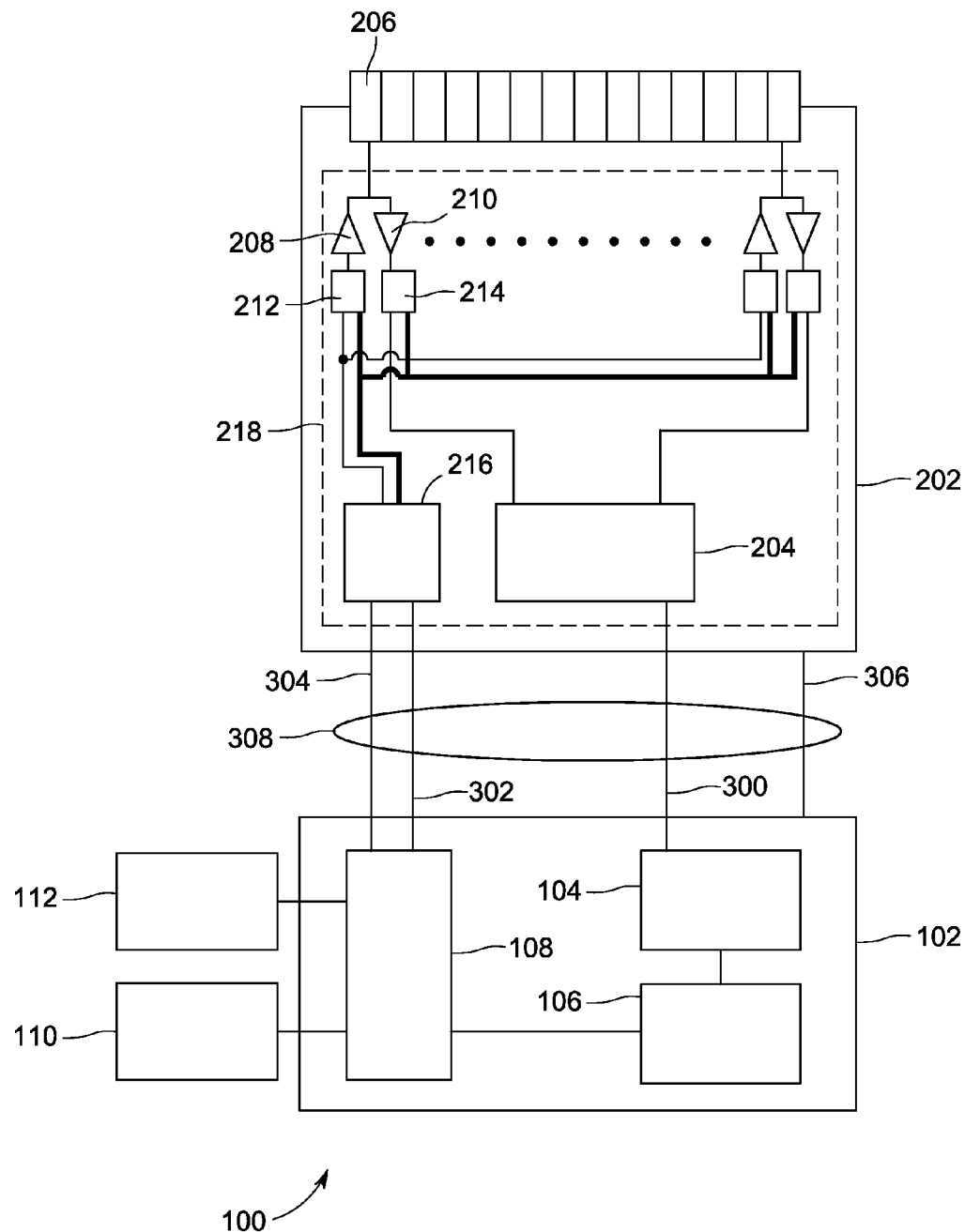
FIG. 1 is a schematic diagram of an exemplary ultrasonic testing system for inspecting a test object.

FIG. 1 depicts an ultrasonic testing system 100 for inspecting a test object. The system 100 comprises a single channel ultrasonic testing unit 102 connected to an ultrasonic probe 202. The single channel ultrasonic testing unit 102 comprises a receiver 104 for receiving a single channel analog signal from the beam former 204 (or summer) of the ultrasonic probe 202. An analog-to-digital converter 106 is also provided for converting the single channel analog signal to a digital signal. The single channel ultrasonic testing unit 102 has a second microprocessor 108 for processing the digital signal.

The ultrasonic probe 202 comprises a plurality of ultrasonic transducers 206, a plurality of electrical pulser circuits 208 used for generating the electrical pulses used to drive the ultrasonic transducers 206, a plurality of amplifiers 210 for receiving and amplifying the electrical signals received from the ultrasonic transducers 206, a plurality of transmit delays 212 connected to the plurality of electrical pulser circuits 208, and a plurality of receive delays 214 connected to the plurality of amplifiers 210. The ultrasonic probe 202 is configured to interrogate a test object from various angles and sequentially relay the data associated with each one of the reflected ultrasonic acoustic wave to single channel ultrasonic testing unit 102. The ultrasonic probe 202 also includes a beam former 204 connected to the plurality of receive delays 214. The ultrasonic probe 202 has a first microprocessor 216, which may include, but is not limited to, a general purpose processor or digital logic such as a field-programmable gate array (FPGA) or an Application Specific Integrated Circuit (ASIC), or a combination thereof. The first microprocessor 216 controls the plurality of electrical pulser circuits 208, the plurality of transmit delays 212, the plurality of amplifiers 210, and the plurality of receive delays 214. In one embodiment, ultrasonic probe 202 is a phased array ultrasonic probe.

Figure 2:
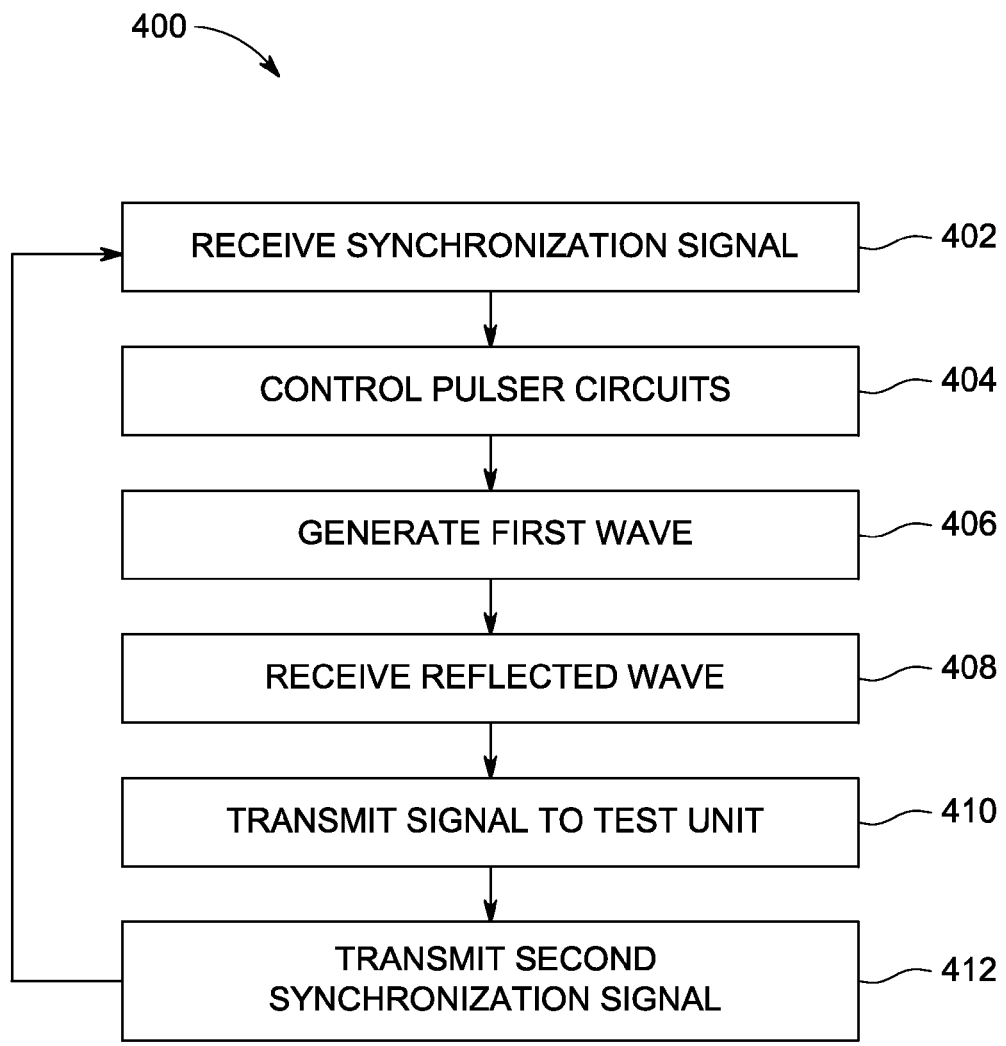
FIG. 2 is a flow diagram depicting an exemplary method of ultrasonic interrogation.

The ultrasonic probe 202 includes a first interface 218 that permits the ultrasonic probe 202 to sequentially transmit data associated with each signal for each angle to the single channel ultrasonic testing unit 102. The technical effect is the ability to install or retrofit a relatively inexpensive single channel ultrasonic testing unit with firmware that makes it capable of nondestructive testing using an ultrasonic probe with multiple ultrasonic transducers. Referring to FIG. 2, in step 402 of exemplary method 400, first microprocessor 216 receives a first synchronization signal from second microprocessor 108. In step 404, the first synchronization signal controls the electrical pulser circuits 208 to interrogate the test object from a first angle. A control signal is sent from first microprocessor 216 of the ultrasonic probe 202 to transmit delays 212, which causes the plurality of ultrasonic transducers 206 to interrogate a test object from a first angle by generating a first ultrasonic acoustic wave in step 406. In step 408, a reflected ultrasonic acoustic wave is received when the emitted ultrasonic acoustic wave interacts with the test object. The reflected ultrasonic signal is converted to an electrical signal by the ultrasonic transducers 206, amplified by the amplifiers 210, delayed by the receive delays 214 and transmitted to the beam former 204. The single channel analog signal output from the beam former 204 is transmitted to the single channel ultrasonic testing unit 102 across the single signal conduit 300 (step 410) and is received by the receiver 104. In one embodiment, receiver 104 includes an amplifier that amplifies the single channel analog signal. Analog-to-digital converter 106 receives the single channel analog signal from the receiver 104 and converts the analog signal to a digital signal. The second microprocessor 108 of the single channel ultrasonic testing unit 102 receives the digital signal which contains data corresponding to the analog signal for, e.g., the first angle.

In step 412, the second microprocessor 108 of the single channel ultrasonic testing unit 102 sends a second synchronization signal back to the first microprocessor 216 of the ultrasonic probe 202, which notifies the ultrasonic probe 202 to proceed to the next angle. Upon receipt of the second synchronization signal, first microprocessor 216 uses a second control signal to control the plurality of electrical pulser circuits 208 to interrogate the test object at the next (second) angle. The newly acquired data is transmitted to the second microprocessor 108 of the single channel ultrasonic testing unit 102 along single signal conduit 300. The single signal conduit 300 is used to transmit the single channel analog signal for all of the angles being measured. For those embodiments where a large number of ultrasonic transducers are used, this single conduit approach utilizes the single signal conduit 300 in a manner that is highly efficient, thereby reducing the total number of lines (or wires) needed. The data associated with each signal for each angle is transmitted from ultrasonic probe 202 to the single channel ultrasonic testing unit 102 sequentially where second microprocessor 108 of the single channel ultrasonic testing unit 102 compiles the data from each signal for each angle to produce and display a sector scan image. Data from the first angle may be stored in memory while data from the second angle is being generated and processed. The sector scan image is continuously updated as data for each signal for each angle arrives at second microprocessor 108 of the single channel ultrasonic testing unit 102. Existing single channel ultrasonic testing units 102 can be retrofitted with a software upgrade to enable the second microprocessor 108 to compile the data from each signal for each angle to produce and display a sector scan image.

In one embodiment, the second microprocessor 108 of the single channel ultrasonic testing unit 102 and the first microprocessor 216 of the ultrasonic probe 202 synchronize with regard to the angle currently selected across a dedicated synchronization conduit 302. In another embodiment, the synchronization occurs across the single signal conduit 300. In certain embodiments, a communications conduit 304 is provided between the second microprocessor 108 of the single channel ultrasonic testing unit 102 and the first microprocessor 216 of the ultrasonic probe 202. Communications conduit 304 provides an additional pathway for sending control signals between the two microprocessors 108, 216. Examples of suitable communication conduits include Universal Serial Bus (USB) and RS232 connections, etc. A power conduit 306 may also be provided. In one embodiment, the conduits connecting the ultrasonic probe 202 and single channel ultrasonic testing unit 102 are bundled into a single probe cable 308.

The single channel ultrasonic testing unit 102 may further include a user interface 110. Examples of suitable user interfaces include keyboard, mouse controllers, touch screens and the like. A display 112 may also be provided for graphically illustrating the sector scan images that result from the ultrasonic interrogation. Display 112 may include a screen or other graphic display. In some embodiments, the user interface 110 and the display 112 may be integral with the single channel ultrasonic testing unit 102. Alternatively, the user interface 110 and the display 112 may be separate elements. In yet another embodiment, one such component is integral while the other is separable.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, radio frequency, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasonic probe comprising:
   a plurality of ultrasonic transducer elements;
   a plurality of electrical pulser circuits for generating and transmitting electrical pulses to the ultrasonic transducer elements;
   a first microprocessor for controlling the plurality of electrical pulser circuits to interrogate a test object from various angles; and a first interface configured to communicate with a single channel ultrasonic testing unit in order to sequentially transmit data associated with each angle to the testing unit.

2. The ultrasonic probe of claim 1, wherein the ultrasonic probe is a phased array ultrasonic probe.

3. The ultrasonic probe of claim 1, wherein the first interface is further configured to transmit a single channel analog signal.

4. The ultrasonic probe of claim 1, wherein the first microprocessor is configured to communicate with a second microprocessor associated with the single channel ultrasonic testing unit, the first microprocessor and the second microprocessor being in communication through a probe cable that connects the ultrasonic probe to the single channel ultrasonic testing unit.

5. The ultrasonic probe of claim 4, wherein the first microprocessor is further configured to communicate at least one of synchronization signals or control signals with the second microprocessor.

6. The ultrasonic probe of claim 1, further comprising a probe cable for connecting the first interface to the single channel ultrasonic testing unit.

7. The ultrasonic probe of claim 6, wherein the probe cable comprises electrical conduits configured to carry a single channel analog signal and at least one of synchronization signals, control signals, or power.

8. A method of ultrasonic inspection comprising:
receiving, by a first microprocessor disposed within an ultrasonic probe, a synchronization signal from a second microprocessor that is disposed within a single channel ultrasonic testing unit, the ultrasonic probe and the single channel ultrasonic testing unit being in communication through a probe cable;
controlling a plurality of electrical pulser circuits in response to the synchronization signal, the plurality of electrical pulser circuits being disposed in the ultrasonic probe;
generating, in a test object, first ultrasonic acoustic waves responsive to each of the plurality of electrical pulser circuits, the first ultrasonic acoustic waves corresponding to a first angle;
receiving first ultrasonic acoustic waves reflected from the test object;
transmitting a first single channel analog signal, representative of the received first ultrasonic acoustic waves, from the ultrasonic probe to the single channel ultrasonic testing unit, wherein the first single channel analog signal is configured to be received by the single channel ultrasonic testing unit;
compiling the first and second single channel analog signals to form a sector scan; and
continuously updating the sector scan image as ultrasonic acoustic waves are sequentially received from different angles.

9. The method of claim 8 further comprising the steps of receiving a second synchronization signal;
controlling the plurality of electrical pulser circuits in response to the second synchronization signal; and
generating, in the test object, second ultrasonic acoustic waves, the second ultrasonic acoustic waves corresponding to a second angle different from the first angle.

10. The method of claim 9 further comprising the steps of receiving second ultrasonic acoustic waves reflected from the test object; and
transmitting a second single channel analog signal, representative of the received second ultrasonic acoustic waves, wherein the second single channel analog signal is configured to be received by the single channel ultrasonic testing unit.

11. The method of claim 8, further comprising the step of displaying the sector scan image on a display.

12. A non-transitory medium storing logic that, when executed, causes a circuit to perform a method comprising:
receiving, by a first microprocessor disposed within an ultrasonic probe, a synchronization signal from a second microprocessor that is disposed within a single channel ultrasonic testing unit, the ultrasonic probe and the single channel ultrasonic testing unit being in communication through a probe cable;
controlling a plurality of electrical pulser circuits in response to the synchronization signal, the plurality of electrical pulser circuits being disposed in the ultrasonic probe;
generating, in a test object, ultrasonic acoustic waves responsive to each of the plurality of electrical pulser circuits;
receiving ultrasonic acoustic waves reflected from the test object; and
transmitting a single channel analog signal, representative of the received ultrasonic acoustic waves from the ultrasonic probe to the single channel ultrasonic testing unit, wherein the single channel analog signal is configured to be received by the single channel ultrasonic testing unit;
compiling the first and second single channel analog signals to form a sector scan; and
continuously updating the sector scan image as ultrasonic acoustic waves are sequentially received from different angles.

* * * * *